United States Patent [19]

Tenerz et al.

[11] Patent Number: 5,694,946
[45] Date of Patent: Dec. 9, 1997

[54] METHOD FOR IN VIVO MONITORING OF PHYSIOLOGICAL PRESSURES

[75] Inventors: Lars Tenerz, Uppsala; Bertil Hoek, Vaesteras; Svante Berg, Maelarbaden, all of Sweden

[73] Assignee: Radi Medical Systems AB, Uppsala, Sweden

[21] Appl. No.: 557,163

[22] PCT Filed: Jun. 23, 1994

[86] PCT No.: PCT/SE94/00636

§ 371 Date: Dec. 20, 1995

§ 102(e) Date: Dec. 20, 1995

[87] PCT Pub. No.: WO95/00071

PCT Pub. Date: Jan. 5, 1995

[30] Foreign Application Priority Data

Jun. 23, 1993 [SE] Sweden ............... 9302183

[51] Int. Cl.⁶ .................................. A61B 5/00
[52] U.S. Cl. .......................... 128/748; 128/782
[58] Field of Search ................... 128/748, 774, 128/782

[56] References Cited

U.S. PATENT DOCUMENTS

| | | | |
|---|---|---|---|
| 4,210,029 | 7/1980 | Porter | 73/705 |
| 4,393,878 | 7/1983 | Kahn | 128/748 |
| 4,517,842 | 5/1985 | Twomey et al. | 73/701 |
| 4,614,118 | 9/1986 | Strickland, Jr. | 73/701 |
| 4,712,566 | 12/1987 | Hoek | 128/748 |
| 5,195,375 | 3/1993 | Tenerz et al. | 73/705 |

FOREIGN PATENT DOCUMENTS

89/09018  10/1989  WIPO.

OTHER PUBLICATIONS

Olsson et al., "Mobility in the Lumbosacral Spine After Fusion Studied with the Aid of Roentgen Stereophotogrammetry", Clinical Orthopaedic and Rel. Resc., pp. 181–190, (1977).

Primary Examiner—Max Hindenburg
Attorney, Agent, or Firm—Foley & Lardner

[57] ABSTRACT

The present invention provides a method of diagnosing damaged intervertebral disks by measuring pressure in a plurality of disks and comparing the different pressures to ascertain the damaged disk. Another method provides for localising a damaged intervertebral disk by measuring pressure in a first disk suspected to be damaged, and measuring the pressure in disks surrounding the suspected disk, comparing the different pressures and diagnosing the damaged disk or simultaneously registering how vertebrae move relative to one another.

8 Claims, 2 Drawing Sheets

METHOD FOR IN VIVO MONITORING OF PHYSIOLOGICAL PRESSURES

The present invention relates generally to measurements of physiological pressures in vivo, and in particular to an apparatus and a method for monitoring rapid dynamic changes in physiological pressures.

It further relates to methods of diagnosing certain painful mechanical disorders of a motion segment in the spine.

BACKGROUND TO THE INVENTION AND PRIOR ART

The spinal column is built up of vertebrae and intervertebral cartilage disks, located between each vertebra. The function of the disks is to accomodate the pressure exerted by the body and acting on the spinal column, and to provide mobility and flexibility to the spine.

A motion segment of the spine is defined as an intervertebral disk and/or the vertebrae belonging to the same plane of motion.

Disabling lower-back pain without pathoanatomical changes, believed to be caused by damaged disks, presents great problems to orthopedic and neurosurgeons, both in terms of localising the site of pain and remedying the problem by surgery.

The surgical remedy consists of so called fusion, which comprises removing a disk at the segment where the pain is believed to occur, and replacing it with bone. This fusion operation leads to the segment in question becoming stiff, but the patient is relieved of the pain.

A specific problem with this type of pain is that no abnormal changes are visible during X-ray investigations. Therefore, the method of localising the damaged segment causing the pain has, to date, comprised local anasthesia in the disk, at the suspected segment. If the patient under such local anasthesia becomes pain-free when performing acts that otherwise would be painful, this is taken as one indication that the correct segment has been localised.

In view of the fact that this method is based on the subjective statements made by the patient, and the subjective judgement of the physician carrying out the investigation, a relatively high percentage of errors in the diagnosis occurs, which could mean that a non-damaged disk is removed. In addition, this method of diagnosing is very tedious, and up to a week of hospitalisation may be required, naturally at a very high cost.

Therefore there exists a need for a quick and reliable, objective method of localising the damaged motion segment in patients exhibiting disabling lower-back pain without pathoanatomical changes.

It is now proposed that the pressure in the cartilage disks may be of significance in providing basic information about causes of this kind of pain, and also for diagnosing purposes.

However, the pressure in the disks is a parameter which is difficult to record because of the high pressures prevailing inside the disks. Such pressure can amount to from 0 to 1000 kPa. Furthermore, the constituent medium inside the disks is a gel-like fluid. Such consistency makes conventional liquid column techniques for measuring pressures very difficult to use. In addition, the requirement on the pressure sensor is that it has a very small outer diameter, in order that it be possible to insert it into the disk without patient trauma.

U.S. Pat. No. 4,393,878 discloses a pressure monitoring method and apparatus for use in the human body. The apparatus includes a pressure sensor of the diaphragm type. The apparatus is based on providing a substantially constant flow of gas to and from the sensor interior. Changes in pressure within the body causes the diaphragm to alternately close and open an exhaust tube which results in an increase or decrease in the pressure within the sensor interior until an equilibrium pressure is reached. The sensor is adapted for use in body cavities such as the cranium. It appears to be a bulky construction and is not suitable for use for the purposes of the present invention.

U.S. Pat. No. 4,517,842 discloses a fluid pressure transducer of the nullbalance type in which a fluid whose pressure is being sensed acts against one face of a diaphragm and a balancing control fluid acts against the opposite face. The transducers according to this patent are particularly well adapted for measurement of pore pressure in earth fills of natural geological environments.

U.S. Pat. No. 4,614,118 discloses a pressure sensing and measurement device which eliminates errors due to compliance and lack of sensitivity. It makes use of a pressure receiving means such as a flexible diaphragm to detect an impinging object. The cell is internally pressurised to a point equal to a value equal to the external pressure. It is stated in said patent that it is used for detection of solids impinging of an object, such as ice on the hull of a ship, or soil on an imbedded foundation pile.

WO-89/09018 discloses a device for measuring the pressure of a liquid for medical use. The device consists of three subassemblies: a detector, an amplifier and recorder. Said device is particularly well suited for measuring the pressure of a liquid injected into a compliant medium, such as a liquid compartment of the articulate type or an intervertebral disc of humans or animals. The invention makes use of liquid column pressure measurements, which, due to the consistency of the gellike medium in the disc, is not suitable for measuring pressure inside the discs themselves.

U.S. Pat. No. 4,210,029 discloses a fiber optic differential pressure sensor. It measures precisely ambient pressure within a confined space, such as blood pressure or intracranial pressure of a human patient, utilising fiber optic lightguides. The focus of this patent is to improve the sensitivity in the measurement of the absolute pressure. The problem of monitoring small fluctuation and rapid dynamic changes overlaying a large pressure is not addressed.

The Technical Problem

The problem that the present invention sets out to solve is to measure in vivo physiological pressures, and in particular rapid dynamic changes in such pressures, where fluctuations occur in a high frequency domain overlaying slower changes of the basal pressure in a low frequency domain, and where the rapid fluctuations vary within an interval in registered pressure which is up to about ten orders of magnitude smaller than the basal pressure prevailing at the site of measurement, such as in the intervertebral disks.

This problem is solved by utilizing one miniature pressure sensor (rapid response, high-frequency domain) for the in vivo measurement, and one pressure sensor external to the measurment point (not necessarily so rapid, but with the capacity to measure high pressures, 0–1000 kPa or more).

In General any measurement system suffers from a limiting signal-to-noise ratio, in addition to a drift in signals which inevitably leads to the sensors outputting erroneous values. By using two sensors as indicated above, and registering the sum of the signals which represents the actual pressure in the measurement point, one achieves much lower drift than if one used a single pressure transducer, measuring over the entire dynamic pressure range (0–1000 kPa). The system also becomes significantly faster than by simply using a pressure transmitting medium, and only measuring the pressure externally of the actual measurment point.

SUMMARY OF THE INVENTION

The present invention provides in one aspect an apparatus for in vivo monitoring of physiologigal pressures, comprising a pressure sensor having a pressure sensing interface, yielding a signal indicative of the pressure differential across said interface; means for pressurising or depressurising the sensor interior in response to a change in the signal from said sensor; pressure measuring means for measuring the pressure supplied by the pressurising means yielding a signal indicative of the pressure in the sensor interior; and means for registering a total pressure as the sum of the signals from said sensor and said pressure measuring means respectively.

In another aspect it provides a method of localising a damaged intervertebral disk, comprising the steps of measuring the pressure in a first disk suspected to be damaged, measuring the pressure in the disks surrounding said suspected disk, preferably simultaneously with the measurements in the first disk, registering whether there is a difference in pressure between the disks, and selecting the disk with a differing pressure to be the damaged disk.

SHORT DESCRIPTION OF THE DRAWINGS

DETAILED DESCRIPTION OF THE PREFERRED EMBODIMENT

Within the context of this application the term "depresurizing" means lowering the pressure.

Figure 1:
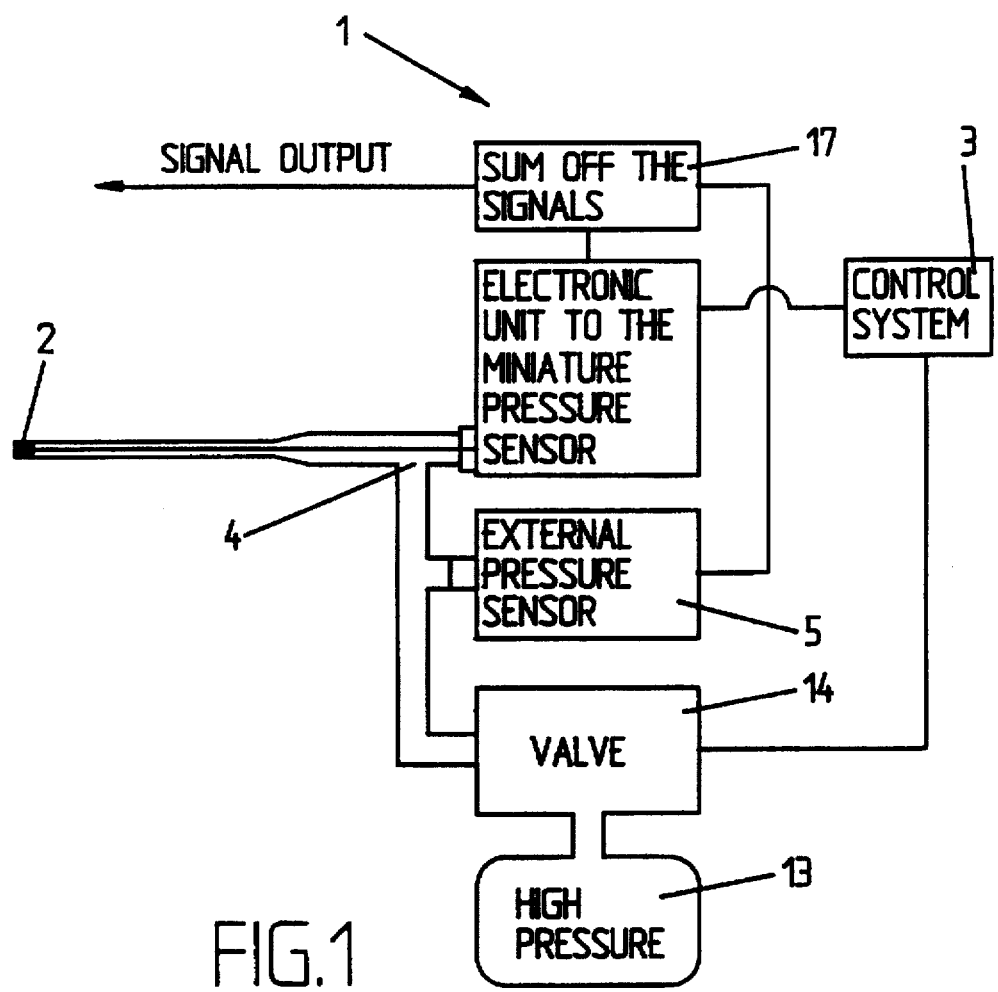
FIG. 1 is an overview of the apparatus according to the invention.

Referring first to FIG. 1, the apparatus, generally designated by the numeral 1, of the invention comprises a differential pressure sensor 2 with a measurment range of typically a tenth of the total measurement range, and a control system 3 for balancing the pressure in a reference channel (air channel) 4 of the sensor 2 over the entire pressure range. The actual pressure at the point of measurment is the sum of the pressure differential across the sensor 2 and the pressure in the reference channel 4, which is measured with an external pressure sensor 5. With this design of the system the rapid changes in pressure are monitored by the differential pressure sensor 2 until the control system 5 has balanced the pressures.

Figure 2:
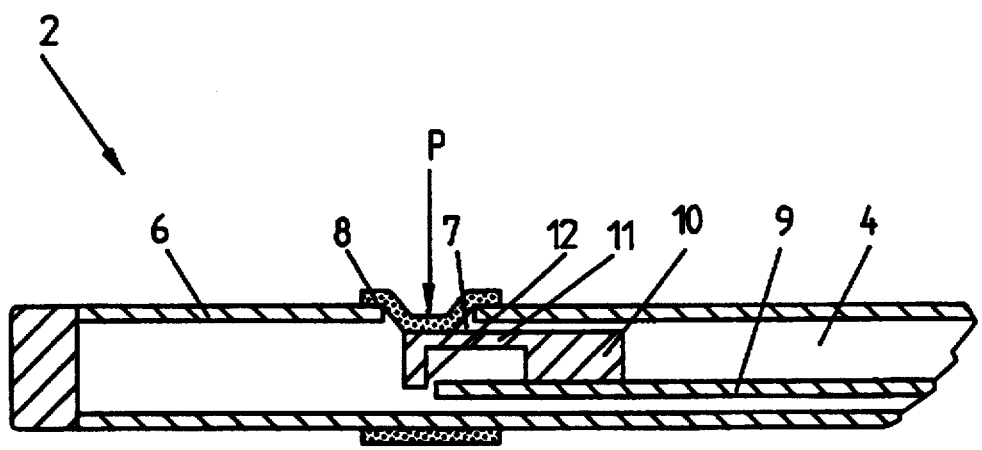
FIG. 2 is detailed view of a membrane sensor suitable for use in the apparatus according to the invention.

With reference now to FIG. 2, there is shown a suitable differential pressure sensor 2. Such a sensor is described in U.S. Pat. No. 5,195,375, and comprises an elastic material shell 6 having an outer surface with an opening 7 extending therethrough. The opening is covered by an elastic diaphragm 8, and a light conductor 9 having an end surface is disposed inside the shell and connected thereto by a glue joint. A body 10 of silicon or gallium is disposed inside the shell and has a thin, cantilevered short beam 11 portion and a reflecting surface 12 connected to and perpendicularly projecting from a free end of the short beam 11 portion. The reflecting surface 12 is proximate to the end surface of the light conductor so that when the diaphragm 8 is subjected to a pressure differential P, it is forced to move thereby causing a corresponding movement of the short beam 11 portion. The sensor 2 is connected at the distal end of a thin catheter or the like, forming an interior air channel 4 in fluid communication with a control system 3 for controlling and balancing the pressures (to be described below).

In this connection it should be emphasized that any pressure sensor capable of detecting a pressure differential across an interface may be utilized in the invention within the scope of the appended claims. E.g. a piezo resistive sensor is a conceiveable alternative.

The control system 3 comprises a PID regulator (Proportional Integrating Differentiating), which gives a faster regulation. One can view the control system as a "comparator", comparing a desired value of the pressure differential between the air channel 4 and the surrounding pressure (ambient), with the actual pressure differential (actual value) across the pressure sensor. The preferred sensor (U.S. Pat. No. 5,195,375) is more sensitive to internal overpressure than underpressure, it could explode if the pressure inside becomes exessive), and therefore the control system 3 operates to maintain a slight underpressure of 200 mm Hg (the cited sensor according to U.S. Pat. No. 5,195, 375 operates within a range of from −25 to +300 mm Hg). Thus, if the desired value e.g. is set to be 200 mm Hg (2670 Pa) and the pressure sensor outputs a signal indicating a higher pressure differential than 200 mm Hg, the pressure in the air channel 4 will be increased. Conversely, if the signal indicates a lower pressure than the desired value, the pressure in the air channel 4 will be lowered. Said pressure can be generated in several ways.

In one embodiment a compressor 13 or alternatively a high pressure gas bottle can be used. A valve 14 connects the outlet of the compressor or bottle with the channel 4. The valve 14 is caused to open or close depending on the pressure differential between the air channel 4 and ambient pressure.

In a second embodiment one utilizes a syringe or pneumatic device, with a piston in a cylinder, controlled by a stepper motor. To increase the pressure the piston is moved in a direction so as to compress the air and vice versa.

In order to obtain the desired information regarding the variations in pressure as a function of the various movements of the patient, the signals from the pressure sensor 2 located in vivo, and from the externally located pressure measuring means 5 measuring the pressure supplied to the interior of the sensor 2 respectively, are summed 17, and the total pressure is recorded on e.g. a chart recorder, or sampled in digital form in a computer for processing and/or display on a screen.

The design of the apparatus according to the invention has several advantages. The external pressure measuring device 5, measuring the static pressure (in the air channel 4) does not have any dimensional limitations, and measures in air under controlled conditions. Further, the dynamic variations can be measured by a microtip sensor 2 in the measurement point, which on one hand provides the capcity to measure signals up to several hundred Hz within the range of the sensor 2, and on the other hand makes the system more rapid, by virtue of the rapid response microtip sensor which compensates for the delay in the control system 3, balancing the pressures.

The stability requirements of the microtip pressure sensor 2 also become less severe than if the entire dynamic pressure range should rest on said sensor. For instance if the microtip pressure sensor measures 10% of the entire pressure range, and has a drift of 10% of the entire range, then the total error in the measurment only becomes 1% (under the condition that the external pressure measuring device 5 gives correct readings).

A practical problem with the system is that if the membrane 8 on the sensor 2 breaks, an overpressure could occur at the measurement point, with air entering at said point. In order to minimize the risk that any larger amounts of air leak out, there are several possible solutions available.

Figure 3:
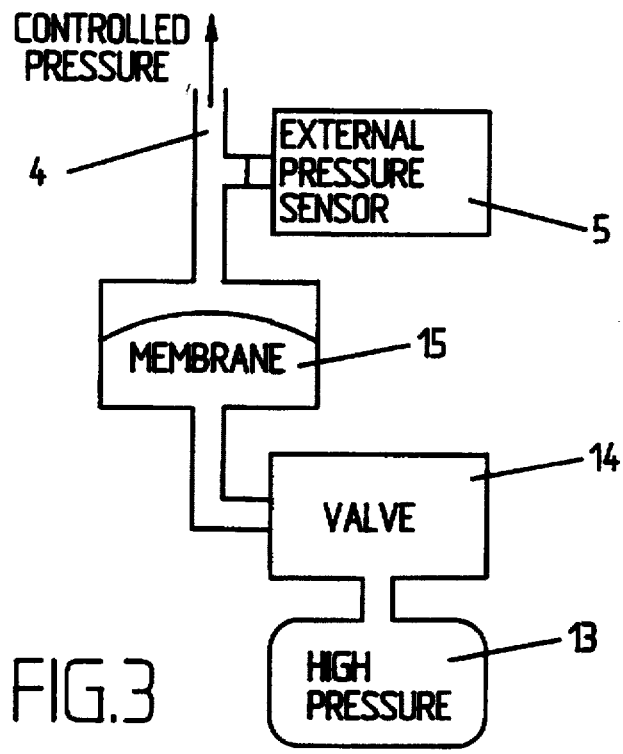
FIG. 3 shows one embodiment of the leakage preventing systems for use with the invention.

First one can limit the maximum amount of air that could leak out, by providing a leak-tight, high pressure-resistant membrane 15 in communication with the air channel 4 communicatinng with the differential microtip pressure sensor 2 (FIG. 3). Such a membrane should have a relatively large area in order to be able to accomodate relatively large pressure changes.

Secondly an oscillating pressure pulse can be supplied by the control system. This is detected by the microtip sensor, which is a confirmation that the membrane is leak tight (if e.g. the pressure inside the sensor is increased by say 10 mm Hg, the pressure differential across the sensor decreases with the same amount). The total pressure is of course constant if the oscillations are slow, since it is the sum of the two signals that is detected by the system and recorded. If the signal on the microtip sensor 2 disappears, a saftey valve is opened to provide atmospheric pressure in the air channel 4.

Figure 4:
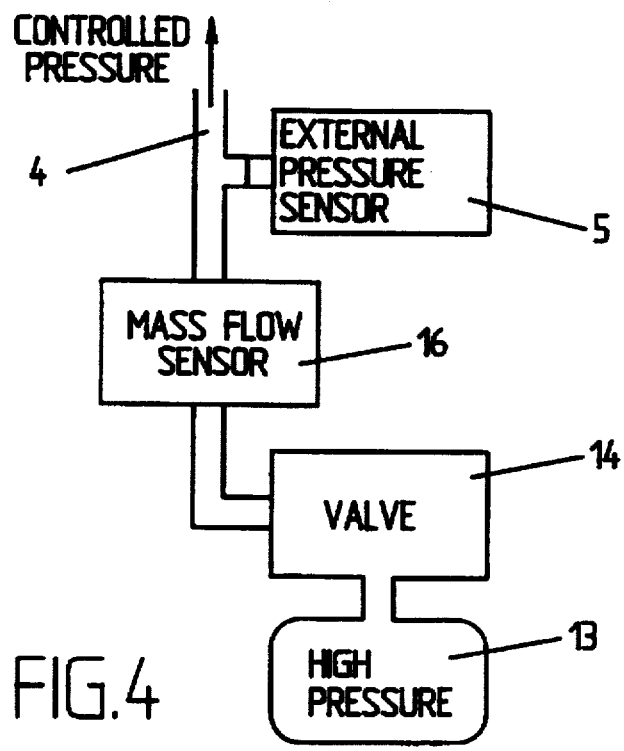
FIG. 4 shows another embodiment of the leakage preventing systems for use with the invention.

Thirdly a mass flow sensor 16 can be provided in the air channel 4 (FIG. 4). Such a sensor 16 would detect any leakage from the sensor tip into the patient. Thereby the mass flow is compared with the pressure increase in the air channel 4. The relation between mass flow and pressure increase is obtained from the general gas equation $$pV=nRT$$

p=pressure V=volume n=number of moles R=gas constant T=temperature
This equation can be rewritten as $$P=(R*T)/V*n=K*n$$

Differentiation with respect to time yields $$dP/dt=K*dn/dt$$

i.e. the rate of change in pressure is proportional to the mass flow.

Thus, by measuring the pressure increase in the air channel 4 and the mass flow, it is possible to detect if the air channel 4 is tight, e.g V=constant. In order to compensate for the individual variations between the sensors 2, it is possible to calibrate each sensor 2 and thus calculate the constant by increasing pressure and measure mass flow.

As already briefly discussed in the preamble, the inventors have discovered that the pressure in the intervertebral disks potentially could be very important in on one hand understanding the fundamental causes of disabling lower-back pain without pathoanatomical changes, and on the other hand to diagnose such syndrom.

Experiments have shown that the pressure in a damaged disk differs from and appears to be significantly lower than in undamaged ones, when the spinal column is under load, i.e. when the patient is upright, sitting, standing or walking. The difference amounts to as much as several hundred kPa.

The investigation is carried out as follows:
The patient lies down and the physician punctures the skin with a needle, and enters it into a disk which is believed to be damaged. Thereafter a microtip sensor, which is connected to the control system, is inserted through the needle.

In view of the small dimensions of the preferred sensor, the needle can also be very thin and the trauma for the patient is minimized during insertion thereof.

After the system is checked for stability, the patient is asked to perform various acts, such as sitting up, standing, walking, turning, twisting the back etc, during which the pressure continously is monitored on a recorder.

As already stated, it turned out that the pressure in a damaged disk apparantly is much lower than in a sound one, and therefor it is now possible to objectively determine exactly on which disk an operation should be carried out.

In a preferred embodiment of the method, the measurements are carried out in three disks simultaneously, shortening the investigation time considerably. An investigation that today may take up to a week, could in principle be completed in 30 minutes with the method and apparatus according to the invention.

In a further aspect of the invention, on can combine pressure measurements as described above, with so called roentgen stereophotogrammetry (see e.g. a paper by T. H. Olsson et al in Clinical Orthopaedics and Related Research, 1977, pages 181–190, entitled "Mobility in the Lumbosacral Spine After Fusion Studied with the Aid of Roentgen Stereophotogrammetry"). The latter method makes possible very exact monitoring of relative motion of the constituents of the skeleton, by implanting small tantalum balls in various locations in the bone, and by a stereo photography technique it is possible to study the motions very accurately. By combining this method with pressure measurements according to the present invention, it would be possible to i.a. obtain information relating to further details of the cause of said lower-back pain, such as pathological changes in disk compliance.

The invention, although essentially described in connection with pressure measurements in intervertebral disks, is suitable for application also in other areas of pressure measurement, both in medical and non-medical areas.

We claim:

1. A method of diagnosing damaged intervertebral disks, comprising: measuring pressures in a plurality of disks, and comparing the different pressures to ascertain the damaged disk.

2. A method of localising a damaged intervertebral disk, comprising the steps of:
    a) measuring the pressure in a first disk suspected to be damaged,
    b) measuring the pressure in the disks surrounding the suspected disk,
    c) comparing any difference in pressure among the disks, and
    d) diagnosing the disk with a differing pressure to be the damaged disk.

3. The method as claimed in claim 2, comprising measuring the pressure in at least two adjacent disks.

4. The method claimed in claim 2, including measuring the pressure of the disks simultaneously.

5. The method as claimed in claim 3, including measuring the pressure in at least three closely adjacent disks.

6. The method as claimed in claim 3, including measuring the pressure in four closely adjacent disks.

7. A method of localising a damaged intervertebral disk, comprising, measuring the pressure in a first disk suspected to be damaged, and simultaneously registering how the vertebrae move relative to each other.

8. The method of claim 7, including registering the vertebrae movement by roentgen stereophotogrammetry.

* * * * *